(12) United States Patent
Jeong et al.

(10) Patent No.: US 10,918,188 B2
(45) Date of Patent: Feb. 16, 2021

(54) COSMETIC PRODUCT COMPRISING SCREEN MESH AND METHOD FOR PRODUCING SAME

(71) Applicant: AMOREPACIFIC CORPORATION, Seoul (KR)

(72) Inventors: Hae Won Jeong, Yongin-si (KR); Kyung Ho Choi, Yongin-si (KR); Kyung Nam Kim, Yongin-si (KR); Min Kyung Sim, Yongin-si (KR); Yeong Jin Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 840 days.

(21) Appl. No.: 14/391,933

(22) PCT Filed: Apr. 12, 2013

(86) PCT No.: PCT/KR2013/003103
§ 371 (c)(1),
(2) Date: Oct. 10, 2014

(87) PCT Pub. No.: WO2013/154394
PCT Pub. Date: Oct. 17, 2013

(65) Prior Publication Data
US 2015/0079862 A1    Mar. 19, 2015

(30) Foreign Application Priority Data

Apr. 13, 2012 (KR) .................. 10-2012-0038492
Apr. 11, 2013 (KR) .................. 10-2013-0039987

(51) Int. Cl.
*A45D 34/00* (2006.01)
*A45D 33/00* (2006.01)
(Continued)

(52) U.S. Cl.
CPC ........... *A45D 34/00* (2013.01); *A45D 33/006* (2013.01); *A61K 8/0204* (2013.01);
(Continued)

(58) Field of Classification Search
CPC .... A45D 2200/1018; A45D 2200/1027; A45D 2200/1036; A45D 33/006; A45D 34/00;
(Continued)

(56) References Cited

U.S. PATENT DOCUMENTS 3,133,309 A * 5/1964 Miles .................. B65D 47/42
                                                                    401/202
3,406,420 A    10/1968 Siemund
(Continued)

FOREIGN PATENT DOCUMENTS

CN         1062122 C      2/2001
CN         101400276      4/2009
(Continued)

OTHER PUBLICATIONS

China Office Action—Chinese Application No. 201380031318.X dated Jun. 28, 2016, citing references listed within.
(Continued)

*Primary Examiner* — Elizabeth C Imani
(74) *Attorney, Agent, or Firm* — Cantor Colburn LLP

(57) ABSTRACT

The present invention provides a cosmetic product and a method for producing same, wherein the cosmetic product comprising a screen mesh includes: one or more materials selected from a group consisting of polyurethane, thermoplastic elastomer (TPE), polyester, polyether, acryl and olefin; and an absorbing material adjacent to the screen mesh. The cosmetic product of the present invention enables a user to appropriately adjust the degree of discharge of contents during use of the contents and to use the residual quantity of the carried contents as much as possible by (Continued)

means of the elasticity of the absorbing material. The cosmetic product of the present invention provides a wide variety of choices of absorbing materials compared with conventional cosmetics in which choices of absorbing materials are restricted by the types and pore sizes of the absorbing materials.

15 Claims, 4 Drawing Sheets

(51) Int. Cl.
    *A61Q 17/04*     (2006.01)
    *A61Q 19/00*     (2006.01)
    *A61K 8/02*     (2006.01)

(52) U.S. Cl.
    CPC ............ *A61K 8/0208* (2013.01); *A61Q 17/04* (2013.01); *A61Q 19/00* (2013.01); *A45D 2200/1018* (2013.01); *A45D 2200/1027* (2013.01); *A45D 2200/1036* (2013.01); *A61K 2800/10* (2013.01); *A61K 2800/87* (2013.01); *Y10T 29/49885* (2015.01); *Y10T 442/10* (2015.04)

(58) Field of Classification Search
    CPC .. A45D 2034/002; A45D 40/08; A45D 34/04; A61K 2800/10; A61K 2800/87; A61K 8/0204; A61K 8/0208; A61Q 17/04; A61Q 19/00; Y10T 29/49885; Y10T 442/10; B65D 83/0055; B65D 25/02
    See application file for complete search history.

(56) References Cited

U.S. PATENT DOCUMENTS

| | | | |
|---|---|---|---|
| 6,047,710 A * | 4/2000 | Irving | A45D 33/006 |
| | | | 132/293 |
| 6,336,763 B1 | 1/2002 | Losier et al. | |
| RE38,398 E | 1/2004 | Gueret | |
| 7,461,992 B2 | 12/2008 | Griffon | |
| 2009/0068240 A1 | 3/2009 | Babe et al. | |
| 2017/0036417 A1 | 2/2017 | Iwata et al. | |

FOREIGN PATENT DOCUMENTS

| | | |
|---|---|---|
| EP | 0528705 | 2/1993 |
| EP | 0790017 | 8/1997 |
| EP | 0970674 | 1/2000 |
| EP | 1454577 A2 | 9/2004 |
| EP | 1593318 A1 | 11/2005 |
| EP | 1994853 | 11/2008 |
| JP | 59193309 | 12/1984 |
| JP | H172818 | 5/1989 |
| JP | 0191423 | 6/1989 |
| JP | H1115419 | 8/1989 |
| JP | 06-127574 | 5/1994 |
| JP | 07-289353 | 11/1995 |
| JP | 09-220117 | 8/1997 |
| JP | 09-262132 | 10/1997 |
| JP | 11000223 | 1/1999 |
| JP | 2011087972 | 5/2011 |
| KR | 10-2000-0013194 | 3/2000 |
| KR | 20-2011-0008787 | 9/2011 |
| TW | 1374207 | 10/2012 |
| TW | I374207 | 10/2012 |
| TW | I1374207 | 10/2012 |
| WO | 2006033559 | 3/2006 |
| WO | 2010106789 A1 | 9/2010 |

OTHER PUBLICATIONS

European Search Report—European Application No. 13775524.5 dated Oct. 14, 2015, citing the enumerated references listed within.
International Search Report—PCT/KR2013/003103 dated Jul. 31, 2013.
Written Opinion—PCT/KR2013/003103 dated Jul. 31, 2013.
Taiwanese Office Action—Taiwanese Application No. 10620031940 dated Jan. 11, 2017, citing CN001062122.
Japanese Office Action-Japanese Application No. 2015-505649 dated Jun. 20, 2017, citing references listed within.
Taiwanese Office Action—Taiwanese Application No. 102113194 dated Jun. 12, 2018, citing the two references listed herein.
Taiwanese Office Action—Taiwanese Application No. 102113194 dated Jun. 12, 2018, citing references listed Hereinin.
European Office Action for corresponding European Patent Application No. 13775524.5 dated Feb. 15, 2018, citing the above references.
Decision of Rejection—Japanese Patent Application 2018-128770 dated Jan. 29, 2020, citing references listed within.

* cited by examiner

[Fig. 1]
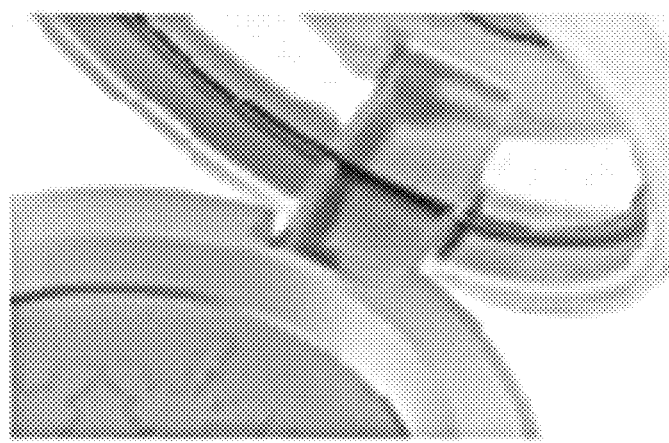
[Fig. 2]
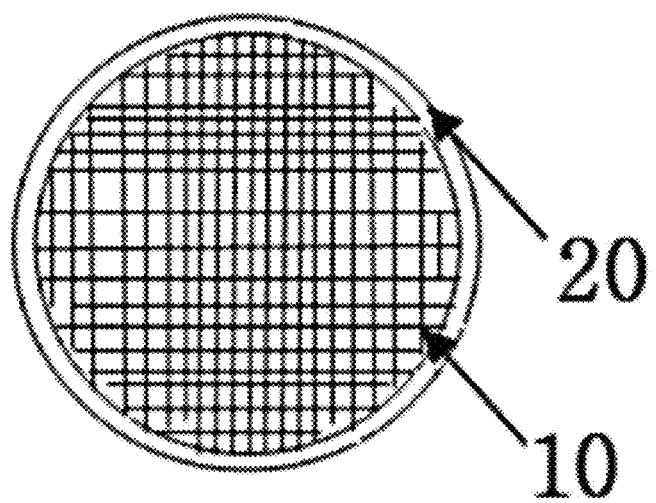

[Fig. 3]
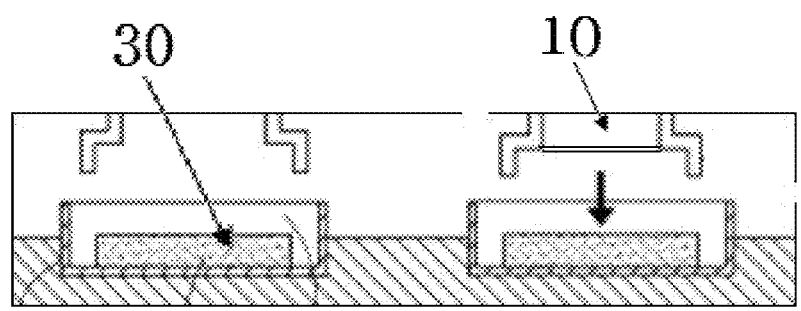
[Fig. 4]
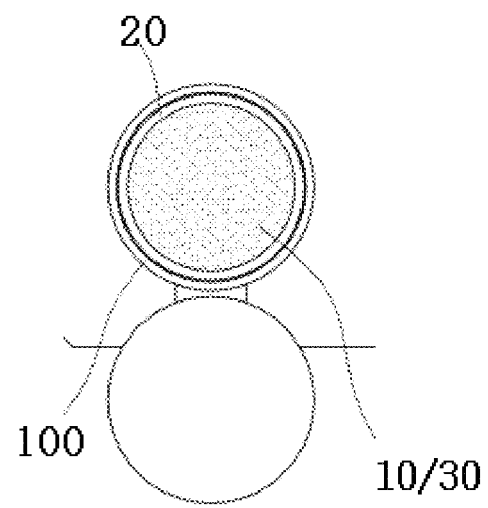

[Fig. 5]
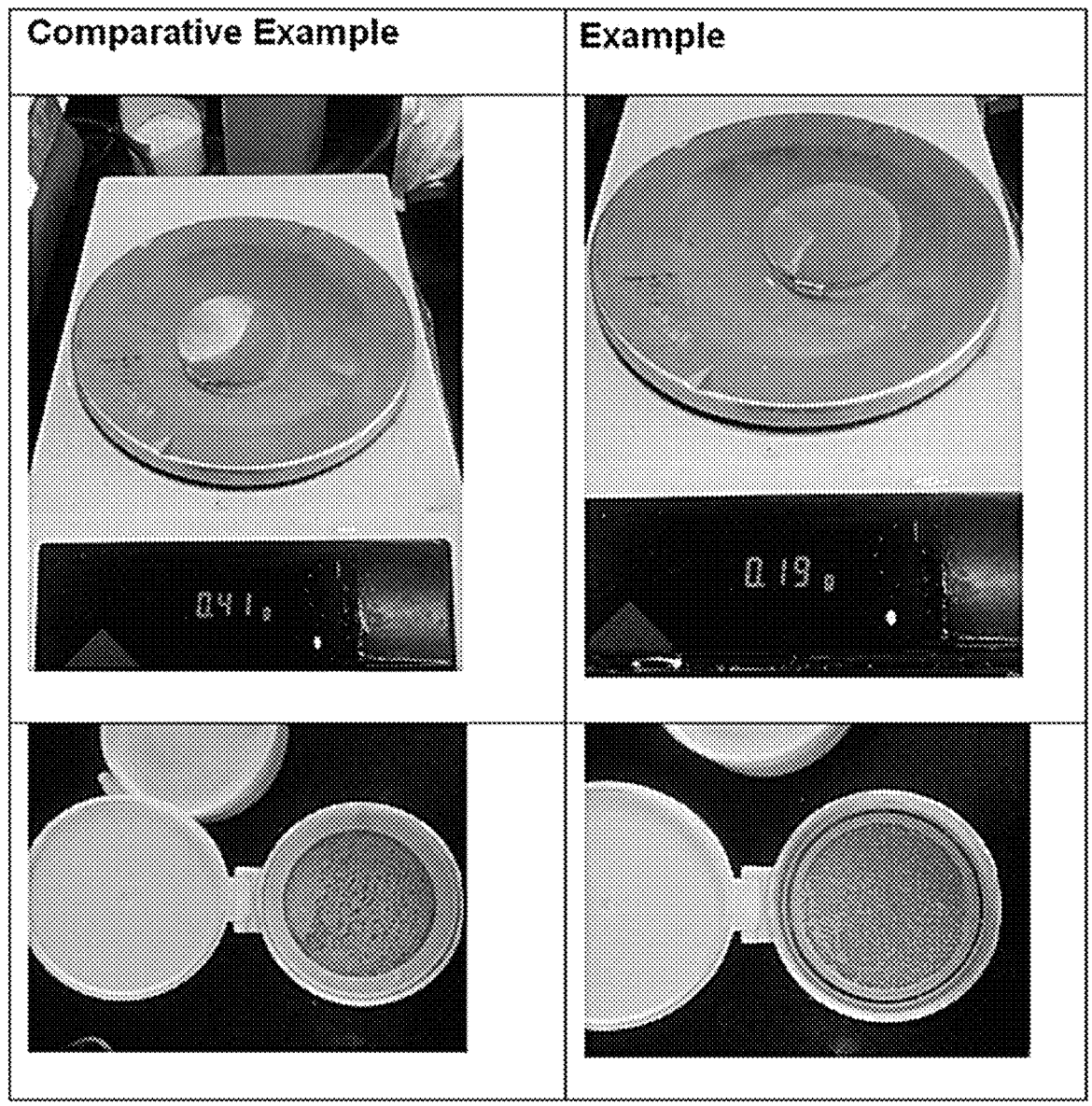

[Fig. 6]
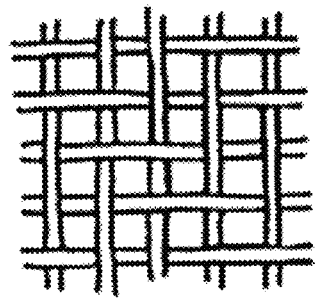
(a) Plain weave
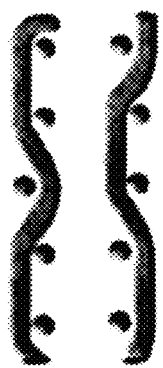
(b) 1:2 and 2:2 Twill
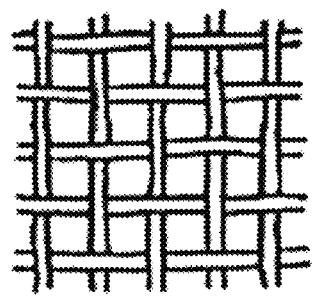
(c) Twill weave
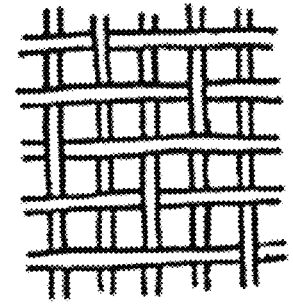
(d) Fancy weave
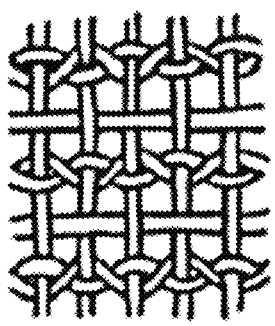
(e) Semi-fancy weave
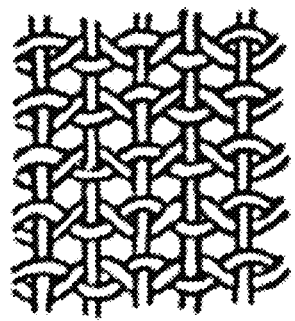
(f) Satin weave

COSMETIC PRODUCT COMPRISING SCREEN MESH AND METHOD FOR PRODUCING SAME

This application is a 371 of PCT/KR2013/003103 filed Apr. 12, 2018.

TECHNICAL FIELD

The present disclosure relates to a cosmetic comprising a screen net and a method for preparing same. More particularly, the present disclosure relates to a cosmetic allowing control of ejection amount of a cosmetic composition via contact between an absorber and a screen net and a method for preparing the same.

BACKGROUND ART

Since most of existing compact products are press compacts containing pressed powder, no additional intermediate structure is necessary. However, a loose powder product wherein unpressed powder is used as it is has a net-type intermediate structure that controls ejection of the content. The net structure usually has a mesh size of 3-5 mm or greater. Since the net structure is to allow the content in powder form to stick to a puff, it should have a mesh size of 3-5 mm or greater. If the mesh size is smaller, the content may not be ejected as desired.

Some anti-UV cosmetics are prepared such that a viscous content is absorbed in an absorber such as a sponge. The extent of absorption of the content by the absorber is dependent on the viscosity of the content and the material, pore size, hardness, etc. of the absorber. The amount of the cosmetic composition that can be used by a customer in the final product may vary depending on these factors. Some products may contain too small an amount of the content as compared to that of the absorber, while others allow use of a relatively large amount of the content.

If an excessively large amount of the content is absorbed in the absorber, the absorber's ability of controlling the ejection of the content is lost. Conversely, if the absorber ejects a relatively small amount of the content, the customers will complain that the amount of the content that can be used is too small. And, some absorbers may swell by reacting with the content, thus resulting in increased volume and mismatch with the container.

Thus, there is a need of a screen net structure that allows use of various absorbers for cosmetics containing liquid contents and is capable of coping with deformation as a result of reaction with the content.

DISCLOSURE

Technical Problem

The present disclosure is directed to providing a cosmetic, in which a liquid content is supported on an absorber using the kneading function of the absorber with the liquid content, that allows control of an ejection amount of the content from the absorber and minimize structural deformation by a screen net adjacent to the absorber and a method for preparing the same.

Technical Solution

In one general aspect, the present disclosure provides a cosmetic comprising: a screen net comprising one or more material selected from a group consisting of polyurethane, thermoplastic elastomer (TPE), polyester, polyether, acryl and olefin; and an absorber adjacent to the screen net.

In an exemplary embodiment of the present disclosure, the screen net may have holes with a size of 0.01-1.0 mm.

In an exemplary embodiment of the present disclosure, the screen net frame may comprise one or more selected from a group consisting of thermoplastic elastomer (TPE), epoxy, acryl, olefin, polyester and polyurethane.

In an exemplary embodiment of the present disclosure, the screen net may be connected to the screen net frame by high-frequency fusion or ultrasonic fusion.

In an exemplary embodiment of the present disclosure, the absorber may be adhered to the screen net or spaced apart therefrom with a distance of 0.1-3.0 mm.

In an exemplary embodiment of the present disclosure, the absorber may be one or more selected from a group consisting of sponge, polyethylene foam, polypropylene foam, polyamide foam, polyester foam, polyether foam, polyurethane foam, cotton, nonwoven, acrylonitrile-butadiene rubber (NBR), styrene-butadiene rubber (SBR), natural rubber (NR), polyvinyl chloride, polyethylene, ethylene-vinyl acetate (EVA), latex, silicone, film type, styrene-isoprene-styrene (SIS), styrene-ethylene-butylene-styrene (SEBS), polyvinyl alcohol (PVA), silicone elastomer, nitrile, butyl, neoprene, dry urethane and wet urethane.

In an exemplary embodiment of the present disclosure, the absorber may absorb a liquid content and an ejection amount of the absorbed liquid content can be controlled by ejecting the liquid content through holes of the screen net.

In another general aspect, the present disclosure provides a method for preparing a cosmetic, comprising: absorbing a liquid content in an absorber; and bringing the absorber adjacent to a screen net.

Advantageous Effects

The cosmetic of the present disclosure allows adequate control of ejection of a content, enables maximum use of the content supported in an absorber and allows use of various types of absorbers which have been limited depending on the type, pore size and etc. In addition, the cosmetic of the present disclosure may provide a fresh feeling as if using a new product by preventing change of the feeling with time.

DESCRIPTION OF DRAWINGS

FIG. 1 shows an existing compact container.

FIG. 2 schematically shows a screen net of a cosmetic according to an exemplary embodiment of the present disclosure.

FIG. 3 schematically shows a cross section of a cosmetic according to an exemplary embodiment of the present disclosure.

FIG. 4 schematically shows a cosmetic according to an exemplary embodiment of the present disclosure.

FIG. 5 shows a test result using a screen net of a cosmetic according to an exemplary embodiment of the present disclosure.

FIG. 6 shows weaving types of a screen net of a cosmetic according to an exemplary embodiment of the present disclosure.

DETAILED DESCRIPTION OF MAIN ELEMENTS

10: screen net
20: screen net frame
30: absorber
100: container

BEST MODE

Hereinafter, exemplary embodiments of the present disclosure will be described in detail with so that those of ordinary skill in the art to which the present disclosure belongs can easily carry out the present disclosure.

The present disclosure provides a cosmetic comprising: a screen net 10 comprising one or more material selected from a group consisting of polyurethane, thermoplastic elastomer (TPE), polyester, polyether, acryl and olefin; and an absorber 30 adjacent to the screen net. Specifically, the present disclosure provides a cosmetic as a cosmetic container accommodating a liquid content comprising: a screen net having holes; and an absorber adjacent to the screen net.

The screen net may further comprise a screen net frame 20 surrounding the screen net.

The cosmetic according to the present disclosure may be prepared by a method for preparing a cosmetic, comprising: absorbing a liquid content in an absorber; and bringing the absorber adjacent to a screen net.

As used herein, the cosmetic refers to a container for accommodating a cosmetic composition or comprises both the container for accommodating the cosmetic composition and the cosmetic composition.

Hereinafter, the method for preparing a cosmetic according to the present disclosure will be described in detail.

First, a liquid content is absorbed in an absorber.

The absorber used in the present disclosure is not particularly limited in material, pore size and etc. For example, the absorber may be one or more selected from a group consisting of sponge, polyethylene foam, polypropylene foam, polyamide foam, polyester foam, polyether foam, polyurethane foam, cotton, nonwoven, acrylonitrile-butadiene rubber (NBR), styrene-butadiene rubber (SBR), natural rubber (NR), polyvinyl chloride, polyethylene, ethylene-vinyl acetate (EVA), latex, silicone, film type, styrene-isoprene-styrene (SIS), styrene-ethylene-butylene-styrene (SEBS), polyvinyl alcohol (PVA), silicone elastomer, nitrile, butyl, neoprene, dry urethane and wet urethane.

In order to use the content absorbed in the absorber as much as possible, it is necessary to increase pore size or reduce hardness of the absorber such that a large amount of the content can be absorbed in the absorber and the absorbed content can be easily ejected. However, if the pore size is too large or if the hardness is too low, the absorber may not maintain its shape and it is difficult to eject the content with a desired amount.

The liquid content used in the present disclosure is not particularly limited as long as the content is in liquid state. For example, the liquid content may be skin lotion, skin softener, skin toner, astringent lotion, milk lotion, moisturizing lotion, nourishing lotion, massage cream, nourishing cream or moisturizing cream, particularly emulsion. Specifically, the liquid content may be an anti-UV agent (sunblock).

The liquid content may be in the form of aqueous, oily, water-in-oil (W/O) or oil-in-water (O/W) emulsion.

The liquid content may have a viscosity of about 1000-20000 CPS. Thus, various liquid contents can be used since the viscosity range is very wide. Accordingly, a variety of kinds of absorbers made of different materials and having different pore sizes, hardnesses, etc. can be used. Therefore, a variety of absorbers that could not be used can be used.

The viscosity of the liquid content can be measured using a viscometer. For example, the viscosity may be measured using LVDV II+PRO or RVDV III ULTRA, spindle No. 63 or spindle No. 64, at 5 rpm or 12 rpm, but is not limited thereto.

The liquid content may be absorbed in the absorber according to a method commonly employed in the art. For example, spraying or squeezing may be employed. Specifically, the content may be absorbed using the kneading function of the absorber with the content.

Subsequently, the absorber is brought adjacent to a screen net.

The absorber may be adhered to the screen net or spaced apart from the screen net with a distance of 0.1-3.0 mm. When the absorber is adhered to the screen net or spaced apart therefrom with a distance of 0.1-3.0 mm, the liquid content absorbed in the absorber may be effectively ejected through the holes of the screen net. If the distance from the screen net exceeds 3.0 mm, the content may not be squeezed when the screen net is pressed and the absorber may not be fixed.

The screen net used in the present disclosure has the following characteristics. 1) Chemical resistance: Swelling, erosion, structural deformation, discoloration, etc. do not occur as a result of reaction with chemicals (alcohols, oils, etc.). 2) Wear resistance: Erosion or permanent deformation does not occur as a result of abrasion by an applicator such as puff, brush, etc. 3) Compatibility with content: Swelling, structural deformation, discoloration, dissolution, pigmentation, etc. do not occur as a result of reaction with the cosmetic substance. 4) Non-toxicity: Environmentally harmful substances such as heavy metals or phthalates are not included.

The weaving type of the screen net of the present disclosure is not particularly limited in structure, shape, number of strands, thickness, material, etc. of threads. For example, the weaving type of the screen net of the present disclosure may be plain weave, 1:2 twill, 2:1 twill, twill weave, fancy weave, semi-fancy weave or satin weave, as shown in FIG. 6.

The screen net is not particularly limited as long as chemical resistance, wear resistance, compatibility with the content and non-toxicity are superior, as described above. Specifically, it may be one or more selected from a group consisting of polyurethane, thermoplastic elastomer (TPE), polyester, polyether, acryl and olefin. The polyester may be an aliphatic polyester resin comprising biodegradable resins such as PLA, PHB, PCL, etc. or an aromatic polyester resin comprising PET, PBT and PEN resins. The shape of the screen net is not particularly limited. It may have circular, polygonal or other shapes depending on the shape of the compact. The fibers that constitute the screen net may have a thickness of specifically 0.01-1.0 mm.

In the cosmetic according to the present disclosure, the force applied to the screen net by a puff (content applicator) is about 400 g·f to 1 kg·f. In general, the force applied to the screen net by the puff is about 400-500 g·f when the screen net is pressed lightly and about 1 kg·f when the screen net is pressed slightly strongly.

Specifically, the screen net may have a percentage of elongation of 1-100% when the screen net is pressed. That is to say, the screen net may be elongated by not greater than 1 cm$^2$ when a unit area of 1 cm$^2$ of the the screen net is pressed vertically. In case of a nylon screen net, which has a percentage of elongation of 200% or greater, pressure is applied only to the pressed portion. In contrast, in case of the screen net according to the present disclosure, which is made of a material selected from a group consisting of polyurethane, thermoplastic elastomer (TPE), polyester, polyether, acryl and olefin, pressure is applied not only to the pressed portion but also to the neighboring portion because the percentage of elongation is smaller than that of nylon. As a result, the absorber is squeezed widely and the content is ejected more widely and uniformly. The screen net according to the present disclosure and one made of nylon are compared in the following table.

TABLE 1

| | Purpose | Constitution | Effect |
|---|---|---|---|
| Nylon | Fixing the content | Consists of fiber and frame. | The content is ejected only at the pressed portion because of high percentage of elongation. |
| Polyurethane, thermoplastic elastomer (TPE), polyester, polyether, acryl or olefin | Fixing the content and allowing uniform ejection of the content | The single material can serve as both of screen net and frame. | The content can be ejected entirely and uniformly, not ejected only at the pressed portion. |

The screen net has holes and the holes may have a size of specifically 0.01-1.0 mm (about 100-10,000 mesh), more specifically 0.5-1.0 mm (about 100-400 mesh), most specifically 0.75-1 mm (about 100-180 mesh). If the hole is smaller than 0.01 mm in size, the particle size of the makeup content becomes very large and the content is not ejected smoothly because of aggregation or surface tension. And, if the hole is larger than 1.0 mm in size, an excessively large amount of the content is ejected. And adequately controlled ejection of the makeup content through the holes of the screen net can be achieved when the holes have a size of the afore-described range.

The preparation method of the present disclosure may further comprise surrounding the screen net with a screen net frame to maintain the structure of the screen net. Specifically, the screen net may be connected to the screen net frame by high-frequency fusion or ultrasonic fusion. FIG. 2 shows the screen net connected to the screen net frame.

The screen net frame may be one or more selected from a group consisting thermoplastic elastomer (TPE), epoxy, acryl, olefin, polyester and polyurethane, although not limited thereto. A screen net frame made of this material is adequate for high-frequency fusion or ultrasonic fusion with the screen net made of the above-described material.

The screen net may be placed inward of a structure fixing the absorber or may be physically engaged with the structure fixing the absorber. Alternatively, the screen net may be coupled with the structure fixing the absorber through double injection or the frame itself may serve as the structure fixing the absorber.

The cosmetic according to the present disclosure allows adequately controlled ejection of the content absorbed in the absorber through the holes of the screen net and allows maximum use of the content. Even when swelling occurs as a result of chemical reaction between the absorber and the content, the screen net adjacent to the absorber maintains the overall structure. Further, since the absorber has elasticity (tension), the user may feel as if using a new product.

In the prepared cosmetic, the absorber absorbs the liquid content and the ejection amount of the absorbed liquid content can be controlled by ejecting the liquid content through holes of the screen net.

Hereinafter, the present disclosure will be described in detail through an example. However, the following example is for illustrative purposes only and it will be apparent to those of ordinary skill in the art that the scope of the present disclosure is not limited by the example.

Test Example 1

Ejection amount of a liquid content was compared for the cases where the screen net according to the present disclosure was used and the existing screen net was used. The result is shown in FIG. 5. A liquid foundation was absorbed in a sponge whose pore size is too large to control the ejection amount of the content. After 5 times of stamping with a puff, 0.41 g of the content was attached to the puff (Comparative Example). When the screen net according to the present disclosure was used for the same cosmetic, the amount attached to the puff decreased by more than 50% to 0.19 g (Example). Thus, it was verified that the ejection of the liquid content can be controlled adequately using the screen net of the present disclosure.

The invention claimed is:

1. A cosmetic comprising:
a screen net comprising one or more material selected from a group consisting of polyurethane, polyester, polyether, and acryl; and
an absorber adjacent to the screen net,
wherein a liquid content is supported on the absorber,
wherein a vertical elongation of the screen net is equal to or less than 1 cm when a force of 400 g·f to 1 kg·f is applied vertically to a unit area (1 cm$^2$) of the screen net, and
the liquid content is ejected to an applicator through the screen net.

2. The cosmetic according to claim 1, wherein the screen net has holes with a size of 0.01-1.0 mm.

3. The cosmetic according to claim 1, wherein the screen net further comprises a screen net frame surrounding the screen net.

4. The cosmetic according to claim 3, wherein the screen net frame comprises one or more selected from a group consisting of thermoplastic elastomer (TPE), epoxy, acryl, olefin, polyester and polyurethane.

5. The cosmetic according to claim 3, wherein the screen net is connected to the screen net frame by high-frequency fusion or ultrasonic fusion.

6. The cosmetic according to claim 1 wherein the absorber is adhered to the screen net or spaced apart therefrom with a distance of 0.1-3.0 mm.

7. The cosmetic according to claim 1, wherein the absorber is one or more selected from a group consisting of sponge, polyethylene foam, polypropylene foam, polyamide foam, polyester foam, polyether foam, polyurethane foam, cotton, nonwoven, acrylonitrile-butadiene rubber (NBR), styrene-butadiene rubber (SBR), natural rubber (NR), polyvinyl chloride, polyethylene, ethylene-vinyl acetate (EVA), latex, silicone, film type, styrene-isoprene-styrene (SIS), styrene-ethylene-butylene-styrene (SEBS), polyvinyl alcohol (PVA), silicone elastomer, nitrile, butyl, neoprene, dry urethane and wet urethane.

8. The cosmetic according to claim 1, wherein the absorber absorbs a liquid content and an ejection amount of the absorbed liquid content can be controlled by ejecting the liquid content through holes of the screen net.

9. A method for preparing a cosmetic, comprising:
absorbing a liquid content in an absorber; and
bringing the absorber adjacent to a screen net,
wherein a vertical elongation of the screen net is equal to or less than 1 cm when a force of 400 g·f to 1 kg·f is applied vertically to a unit area (1 cm$^2$) of the screen net,
the liquid content is ejected to an applicator through the screen net, and
wherein the screen net comprises one or more selected from a group consisting of polyurethane, polyester, polyether, and acryl.

10. The method for preparing a cosmetic according to claim 9, wherein the screen net further comprises a screen net frame surrounding the screen net.

11. The method for preparing a cosmetic according to claim 10, wherein the screen net has holes with a size of 0.01-1.0 mm and is connected to the screen net frame by high-frequency fusion or ultrasonic fusion.

12. The method for preparing a cosmetic according to claim 10, wherein the screen net frame comprises one or more selected from a group consisting of thermoplastic elastomer (TPE), epoxy, acryl, olefin, polyester and polyurethane.

13. The method for preparing a cosmetic according to claim 9, wherein said bringing the absorber adjacent to the screen net comprises adhering the absorber to the screen net or bringing the absorber adjacent to the screen with a distance of 0.1-3.0 mm.

14. The method for preparing a cosmetic according to claim 9, wherein the absorber is one or more selected from a group consisting of sponge, polyethylene foam, polypropylene foam, polyamide foam, polyester foam, polyether foam, polyurethane foam, cotton, nonwoven, acrylonitrile-butadiene rubber (NBR), styrene-butadiene rubber (SBR), natural rubber (NR), polyvinyl chloride, polyethylene, ethylene-vinyl acetate (EVA), latex, silicone, film type, styrene-isoprene-styrene (SIS), styrene-ethylene-butylene-styrene (SEBS), polyvinyl alcohol (PVA), silicone elastomer, nitrile, butyl, neoprene, dry urethane and wet urethane.

15. The method for preparing a cosmetic according to claim 9, wherein an ejection amount of the liquid content absorbed in the absorber can be controlled by ejecting the liquid content through holes of the screen net.

* * * * *